United States Patent
Yamashita et al.

(10) Patent No.: US 11,116,455 B2
(45) Date of Patent: Sep. 14, 2021

(54) DIAGNOSTIC ASSISTANCE DEVICE, VITAL SIGNS INFORMATION MEASURING DEVICE, AND DIAGNOSTIC ASSISTANCE METHOD

(71) Applicant: OMRON HEALTHCARE CO., LTD., Muko (JP)

(72) Inventors: Shingo Yamashita, Muko (JP); Naoki Maeda, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 342 days.

(21) Appl. No.: 16/142,495

(22) Filed: Sep. 26, 2018

(65) Prior Publication Data
US 2019/0021678 A1    Jan. 24, 2019

Related U.S. Application Data

(63) Continuation of application No. PCT/JP2017/012452, filed on Mar. 27, 2017.

(30) Foreign Application Priority Data

Apr. 5, 2016   (JP) .............................. JP2016-075968

(51) Int. Cl.
*A61B 5/0205*   (2006.01)
*A61B 5/00*   (2006.01)
(Continued)

(52) U.S. Cl.
CPC ............ *A61B 5/7282* (2013.01); *A61B 5/022* (2013.01); *A61B 5/0205* (2013.01); *A61B 5/746* (2013.01);
(Continued)

(58) Field of Classification Search
None
See application file for complete search history.

(56) References Cited

U.S. PATENT DOCUMENTS 8,838,217 B2    9/2014   Myr
2008/0294348 A1   11/2008   Tanaka et al.
(Continued)

FOREIGN PATENT DOCUMENTS

CN    101185569 A    5/2008
CN    101416193 A    4/2009
(Continued)

OTHER PUBLICATIONS

Jun. 27, 2017 Search Report issued in International Patent Application No. PCT/JP2017/012452.
(Continued)

*Primary Examiner* — Eric F Winakur
*Assistant Examiner* — Marjan Fardanesh
(74) *Attorney, Agent, or Firm* — Oliff PLC (57) ABSTRACT

A diagnosis assistance device assists a diagnosis, by using a plurality of sets of biological information that are measured from a subject, and that are stored in a storage medium. The diagnosis assistance device includes an achievement status determining section and a notification processing section. The achievement status determining section determines an achievement status of a predetermined condition related to biological information that is measured from the subject, based on the plurality of sets of biological information stored in the storage medium. The notification processing section performs a process of notifying of the achievement status. The condition is that the pattern of a change of biological information which is stored in the storage (Continued)

medium contains, threshold or more times, a specific pattern. The specific pattern is extreme-dipper, non-dipper, or riser.

8 Claims, 7 Drawing Sheets

(51) Int. Cl.
  *A61B 5/022* (2006.01)
  *A61B 5/021* (2006.01)
  *A61B 5/024* (2006.01)

(52) U.S. Cl.
  CPC ....... *A61B 5/02108* (2013.01); *A61B 5/02416* (2013.01); *A61B 5/02444* (2013.01)

(56) References Cited

U.S. PATENT DOCUMENTS

| | | |
|---|---|---|
| 2009/0264773 A1 | 10/2009 | Kishimoto et al. |
| 2010/0113943 A1 | 5/2010 | Burnes et al. |
| 2010/0268098 A1 | 10/2010 | Ito et al. |
| 2011/0144918 A1 | 6/2011 | Inoue |
| 2011/0161107 A1 | 6/2011 | Goldberg et al. |
| 2014/0052008 A1 | 2/2014 | Kim et al. |
| 2014/0077945 A1 | 3/2014 | Amagai |
| 2014/0276123 A1* | 9/2014 | Yang ................ G16H 40/63 600/483 |
| 2015/0038857 A1 | 2/2015 | Yamamoto et al. |

FOREIGN PATENT DOCUMENTS

| | | |
|---|---|---|
| CN | 101925329 A | 12/2010 |
| CN | 104135916 A | 11/2014 |
| CN | 104997498 A | 10/2015 |
| JP | 2007-215722 A | 8/2007 |
| JP | 2008-206920 A | 9/2008 |
| JP | 2010-088576 A | 4/2010 |
| JP | 2010-148712 A | 7/2010 |
| JP | 2014-054479 A | 3/2014 |
| WO | 2007/058128 A1 | 5/2007 |
| WO | 2007/117719 A2 | 10/2007 |

OTHER PUBLICATIONS

Apr. 12, 2018 International Preliminary Report on Patentability issued in International Patent Application No. PCT/JP2017/012452.
Suzuki, Ryoji et al., "Sleep Disturbance Is Associated With Decreased Daily Activity and Impaired Nocturnal Reduction of Blood Pressure in Dementia Patients", Archives of Gerontolog and Geriatrics, Elsevier, Amsterdam, NL, vol. 53, No. 3, Aug. 7, 2010 (Aug. 7, 2010), pp. 323-327.
Oct. 18, 2019 Extended Search Report issued in European Patent Application No. 17778996.3.
Feb. 25, 2020 Office Action issued in Japanese Patent Application No. 2016-075968.
Kario, Kazuomi, "Diurnal blood pressure variation and stroke," Dai 33 kai Nihon Nosocchu Gakkai Koen, 2008, vol. 30, No. 6, pp. 931-937.
Sep. 14, 2020 Office Action issued in Chinese Patent Application No. 201780020475.9.

* cited by examiner

DIAGNOSTIC ASSISTANCE DEVICE, VITAL SIGNS INFORMATION MEASURING DEVICE, AND DIAGNOSTIC ASSISTANCE METHOD

CROSS REFERENCE TO RELATED APPLICATIONS

This application is a continuation of PCT application No. PCT/JP2017/012452, which was filed on Mar. 27, 2017 based on Japanese Patent Application (No. 2016-075968) filed on Apr. 5, 2016, the contents of which are incorporated herein by reference.

BACKGROUND OF THE INVENTION

1. Field of the Invention

The present invention relates to a diagnosis support device, a biological information measurement device, a diagnosis assistance method, and a diagnosis assistance program.

2. Description of the Related Art

Usually, biological information which is necessary for a diagnosis of a living body, such as blood pressure information, pulse information, or beat information has a large circadian variation. In order to perform a diagnosis or the like, therefore, biological information is consecutively measured from the subject, and then recorded.

Patent Literature 1 discloses a biological information measurement device in which blood pressure information is continuously measured a plurality of times by using the oscillometric method, and, after the plurality of measurements of blood pressure information, reliability degrees indicating the reliabilities of the respective sets of measured blood pressure information are displayed.

Patent Literature 2 discloses an activity meter which has a function of measuring the heart rate, and which, at the end of the measurement, displays a trend graph of the heart rate.

Patent Literature 1: JP-A-2010-88576
Patent Literature 2: JP-A-2007-215722

SUMMARY OF THE INVENTION

According to an embodiment of the present invention, there is provided a diagnosis assistance device for assisting a diagnosis which is performed by using a plurality of sets of biological information that are measured from a subject, and that are stored in a storage medium, the diagnosis assistance device comprising:

an achievement status determining section which determines an achievement status of a predetermined condition related to biological information that is measured from the subject, based on the plurality of sets of biological information stored in the storage medium; and a notification processing section which performs a process of notifying of the achievement status, wherein the condition is that the pattern of a change of biological information which is stored in the storage medium contains, threshold or more times, a specific pattern, and the specific pattern is extreme-dipper, non-dipper, or riser.

According to an embodiment of the present invention, there is provided a biological information measurement device which measures biological information, and which stores the biological information in a storage medium, wherein the biological information measurement device includes a diagnosis support device for supporting a diagnosis which is performed by using a plurality of sets of biological information that are measured from a subject, and that are stored in a storage medium, the diagnosis support device including:

an achievement status determining section which determines an achievement status of a predetermined condition related to biological information that is measured from the subject, based on the plurality of sets of biological information stored in the storage medium; and a notification processing section which performs a process of notifying of the achievement status, the biological information measurement device further includes a scheduled-visit-day change determining section which acquires information of a scheduled hospital visit day of the subject from a storage medium that stores the information of the scheduled hospital visit day, and which determines whether the scheduled hospital visit day is required to be changed or not, based on the information and the achievement status, and the notification processing section further notifies of a result of the determination by the scheduled-visit-day change determining section, in addition to the achievement status.

According to an embodiment of the present invention, there is provided a diagnosis assistance method for assisting a diagnosis which is performed by using a plurality of sets of biological information that are measured from a subject by a biological information measurement device, and that are stored in a storage medium, the diagnosis assistance method comprising:

an achievement status determining step of determining an achievement status of a predetermined condition related to biological information that is measured from the subject, based on the plurality of sets of biological information stored in the storage medium; and a notification processing step of performing a process of notifying of the achievement status, wherein the condition is that the pattern of a change of biological information which is stored in the storage medium contains, threshold or more times, a specific pattern, and the specific pattern is extreme-dipper, non-dipper, or riser.

According to an embodiment of the present invention, there is provided a non-transitory computer-readable storage medium, which includes a diagnosis assistance program for assisting a diagnosis which is performed by using a plurality of sets of biological information that are measured from a subject by a biological information measurement device, wherein the program causes a computer to execute:

an achievement status determining step of determining an achievement status of a predetermined condition related to biological information that is measured from the subject, based on the plurality of sets of biological information stored in the storage medium; and a notification processing step of performing a process of notifying of the achievement status, wherein the condition is that the pattern of a change of biological information which is stored in the storage medium contains, threshold or more times, a specific pattern, and the specific pattern is extreme-dipper, non-dipper, or riser.

DETAILED DESCRIPTION OF THE EXEMPLARY EMBODIMENTS

Preferably, biological information such as above-described one which has a large circadian variation is measured in a manner that the subject periodically uses a biological information measurement device in the home of the subject, or the like.

For example, the doctor designates a plurality of specific times (the time of awakening, daytime, before bedtime, and the like) in one day, and the subject uses a biological information measurement device for a plurality of days in the home, and measures biological information at each of the plurality of designated times.

When all of the measurements of biological information at the timings designated by the doctor are ended, the subject carries the biological information measurement device to the hospital. In the hospital, the doctor checks the biological information for the plurality of days which is stored in the biological information measurement device, and determines the treatment strategy.

In such a use mode, there is a possibility that the biological information measurement device is carried to the hospital in a state where samples of biological information the number of which is necessary for determination of the treatment strategy have not been measured. As a result, a diagnosis cannot be correctly performed, or the subject is again requested to measure deficient information in order to correctly perform a diagnosis, and the diagnosis requires a long time. Patent Literatures 1 and 2 fail to consider these problems.

The invention has been conducted in view of the above circumstances. It is an object of the invention to provide a diagnosis assistance device, biological information measurement device, diagnosis assistance method, and diagnosis assistance program which enable the subject to check whether information necessary for a diagnosis is accumulated or not, and which can assistance a prompt and correct diagnosis.

Hereinafter, embodiments of the invention will be described with reference to the drawings.

Figure 1:
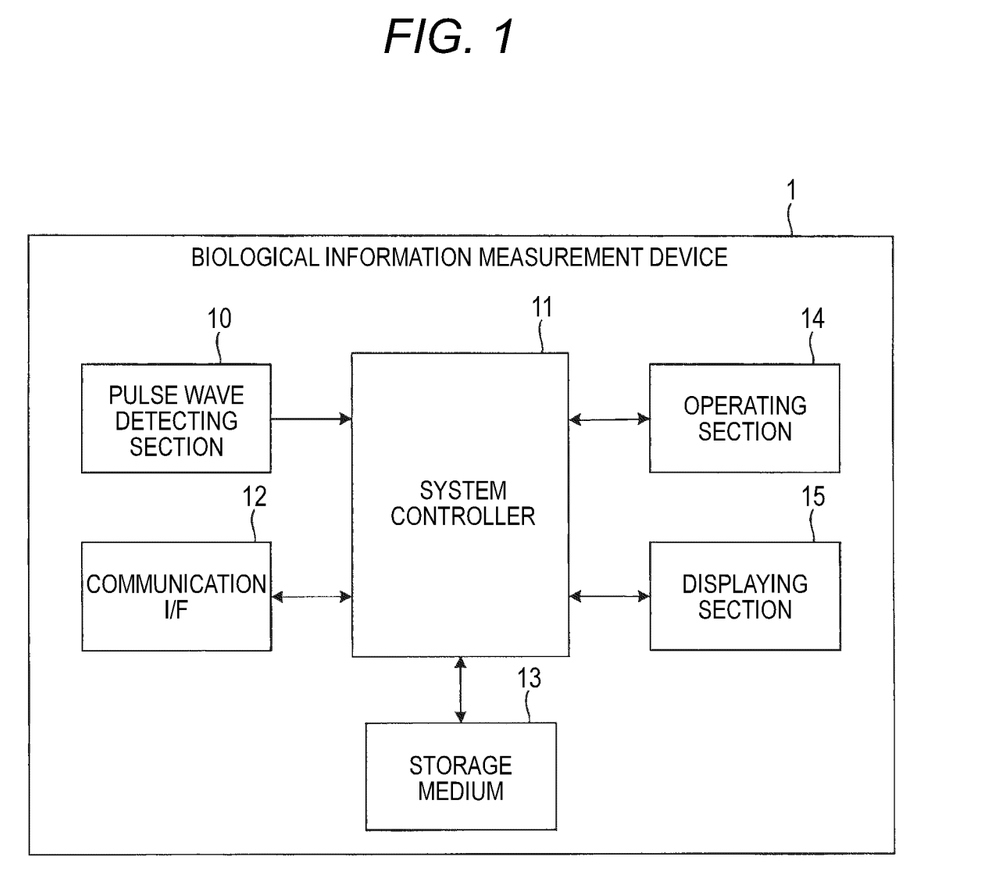
FIG. 1 is a diagram showing the internal hardware configuration of a biological information measurement device 1 for illustrating an embodiment of the invention.

FIG. 1 is a diagram showing the internal hardware configuration of a biological information measurement device 1 for illustrating an embodiment of the invention.

The biological information measurement device 1 measures biological information such as blood pressure information, pulse information, or beat information, and stores the biological information in a storage medium 13. For example, the blood pressure information contains the systolic blood pressure, the diastolic blood pressure, or the mean blood pressure. For example, the pulse information contains the pulse rate and the like. For example, the beat information contains the beat rate and the like.

The biological information measurement device 1 includes a pulse wave detecting section 10, a system controller 11 which generally controls the entire device, a communication interface (I/F) 12, the storage medium 13, an operating section 14, and a displaying section 15.

The pulse wave detecting section 10 detects a pulse wave from a living body portion (such as the wrist) of the subject. In the pulse wave detecting section 10, a configuration which detects a pressure pulse wave as the pulse wave by, for example, using the tonometry method is used. Alternatively, the pulse wave detecting section 10 may detect a volume pulse wave as the pulse wave. The pulse wave detecting section 10 may detect the pulse wave from reflected light from the artery which is obtained by irradiating the artery with a light beam.

The pulse wave detecting section 10 detects a pulse wave which is generated every pulse (the time period when the heart pulsates one time), and supplies the detected pulse wave to the system controller 11.

The system controller 11 is configured mainly by a processor, and includes a ROM (Read Only Memory) which stores programs and the like to be executed by the processor, a RAM (Random Access Memory) functioning as a work memory, and the like.

The system controller 11 calculates biological information based on the pulse wave which is detected every pulse by the pulse wave detecting section 10, and stores the calculated biological information in the storage medium 13 while associated with date information indicating the year, month, and day when the pulse wave is detected, and time information indicating the time when the pulse wave is detected.

The communication I/F 12 is an interface connecting the device to other electronic devices (for example, a hospital terminal disposed in a hospital) by wire or over the wireless.

The storage medium 13 stores various data such as the biological information calculated by the system controller 11. The storage medium 13 is configured by, for example, a flash memory or a hard disk. The storage medium 13 may be a portable storage medium which is detachable from the biological information measurement device 1.

When the operating section 14 is operated, arbitrary information can be stored in the storage medium 13. Information of the scheduled hospital visit day of next visiting the hospital which the subject who measures biological information by using the biological information measurement device 1 visits, and that of a predetermined condition of information which is necessary for a diagnosis is stored as the arbitrary information in the storage medium 13.

The information of the scheduled hospital visit day is date information indicating the year, the month, and the day, and supplied by the subject or a person concerned with the hospital to the biological information measurement device 1, and then stored in the storage medium 13.

The information of the condition is supplied by a person concerned with the hospital, such as the doctor or the nurse to the biological information measurement device 1, and then stored in the storage medium 13 to be set in the device.

Specific examples (first to fifth conditions) of the above-described condition are listed as follows.

The first condition is "The number of sets of biological information which are stored in the storage medium 13 from an arbitrary timing functioning as a reference becomes equal to or larger than a threshold TH1."

As the threshold TH1, an adequate value (for example, 100,000 sets) which is necessary for determination of the treatment strategy for the subject is set by the doctor or the like in consideration of a result of a medical interview with the subject, a test result, and the like. As the arbitrary timing, for example, the year, month, day, and time when the subject undergoes consultation are set by a person concerned with the hospital.

The second condition is "The number of groups of biological information for one day which are stored in the storage medium 13 from the arbitrary timing functioning as the reference becomes equal to or larger than a threshold TH2."

The group of biological information for one day is configured by a plurality of sets of biological information in which sets of information of the same date are stored while associated with one another. When one day is divided into a plurality of periods (for example, 3 divisions or morning, daytime, and night, or 23 divisions in the unit of hour), the group contains, for each of the periods, a predetermined number (a value 1 or more) of sets of biological information corresponding to the day and time belonging to the period.

When at least one measurement of biological information is performed every hour in the same date, for example, a group containing all sets of biological information corresponding to the date is a group of biological information for one day.

The second condition is set, for example, in the case where a change of biological information for one week or one month is to be known.

The first condition and the second condition are conditions for the numbers of sets of biological information stored in the storage medium 13, respectively.

The third condition is "In biological information which is stored in the storage medium 13 from the arbitrary timing functioning as the reference, when seen in time sequence, the occurrence frequency of a first pattern (so-called surge) in which biological information temporarily rises to or higher than a reference value, or the variation amount of biological information is temporarily equal to or larger than a variation threshold is equal to or larger than a threshold TH3."

The term of temporarily means a short predetermined period which is about several seconds to several tens of seconds. As the reference value, the variation threshold, and the threshold TH3, values at which attention is required in the health condition of the subject are set by the doctor. The occurrence frequency indicates the number at which the above-described first pattern occurs in a predetermined period (for example, one day).

The fourth condition is "Change patterns of the biological information which is stored in the storage medium 13 from the arbitrary timing functioning as the reference contain a specific pattern a number of times equal to or larger than a threshold TH4." As the threshold TH4, a value corresponding to a result of a medical interview with the subject, a test result, or the like is set by the doctor.

The specific pattern contains one of the above-described first pattern, and the below-described second pattern.

The second pattern means a pattern of a change of biological information for one day in the case where biological information is blood pressure information, and contains a so-called riser pattern, a so-called non-dipper pattern, a so-called extreme-dipper pattern, or the like.

Extreme-dipper is a pattern in which the decreasing rate of biological information in a predetermined time interval in the night, with respect to biological information in a predetermined time interval in the daytime is 20% or more.

Non-dipper is a pattern in which the decreasing rate of biological information in a time interval in the night, with respect to biological information in a time interval in the daytime is smaller than 10%.

A pattern which is non-dipper, and in which biological information in a time interval in the night rises with respect to biological information in a time interval in the daytime is riser.

The specific pattern is determined as a pattern according to the subject, in accordance with a result of a medical interview with the subject, a test result, and the like.

The third condition and the fourth condition are conditions for a change pattern of biological information stored in the storage medium 13, respectively.

The fifth condition is "Biological information which is stored in the storage medium 13 from the arbitrary timing functioning as the reference contains biological information in which the absolute value is equal to or larger than a threshold TH5." As the threshold TH5, a value at which attention is required in the health condition of the subject is set by the doctor. For example, the fifth condition is set in the case where consultation must be immediately performed, such as a case where an abnormally high blood pressure is measured.

The operating section 14 is an interface for inputting an instruction signal for the system controller 11, and configured by, for example, buttons or touch panel for instructing start, end, and the like of various operations including measurement of biological information.

The displaying section 15 is used for displaying various information such as measured biological information, and configured by a liquid crystal display device or the like.

Figure 2:
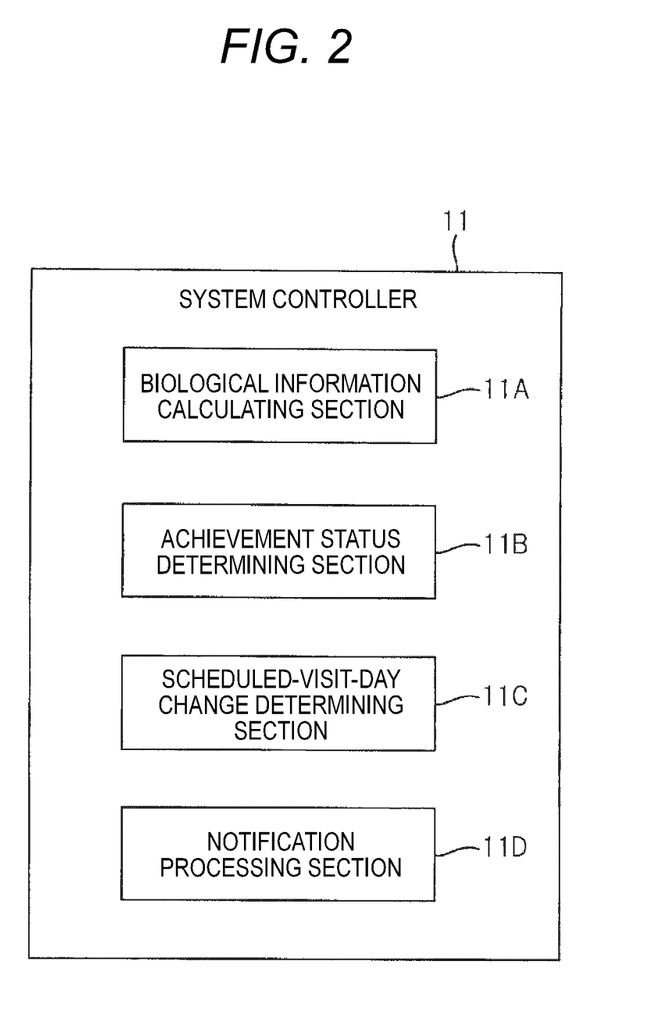
FIG. 2 is a functional block diagram of a system controller 11 of the biological information measurement device 1 shown in FIG. 1.

FIG. 2 is a functional block diagram of the system controller 11 of the biological information measurement device 1 shown in FIG. 1.

The system controller 11 includes a biological information calculating section 11A, an achievement status determining section 11B, a scheduled-visit-day change determining section 11C, and a notification processing section 11D. The system controller 11 constitutes the diagnosis assistance device.

The biological information calculating section 11A, the achievement status determining section 11B, the scheduled-visit-day change determining section 11C, and the notification processing section 11D are configured by causing the processor to execute the programs stored in the ROM. The programs include the diagnosis assistance program.

The biological information calculating section 11A calculates biological information by a well-known method based on the pulse wave supplied from the pulse wave detecting section 10. The biological information calculating section 11A causes the calculated biological information, and information of the date and time at which the pulse wave that is used in the calculation of the biological information is detected, to be stored in the storage medium 13 while associated with one another. In the storage medium 13, the storage of biological information for each beat advances. The biological information calculating section 11A may calculate and store biological information one time per plural beats.

In the case where a predetermined determination condition is satisfied, the achievement status determining section 11B determines the achievement status of the above-described condition stored in the storage medium 13, based on the biological information stored in the storage medium 13. Specifically, the achievement status determining section 11B outputs, as information indicating the achievement status, an achievement rate indicating the degree at which the biological information stored in the storage medium 13 achieves the above-described condition.

The achievement status determining section 11B analyzes the plurality of sets of biological information which are stored in the storage medium 13, and which are arranged in time sequence, obtains the total number of the plurality of sets of biological information, that of groups for one day which are contained in the plurality of sets of biological information, the occurrence frequency of the first pattern, the total number of occurrences of the first pattern, and that of occurrences of the second pattern, and, in accordance with the obtained information, determines the achievement status of the condition.

For example, the above-described determination condition is a case where the end of the measurement of biological information is instructed, for example, by pressing a measurement end button included in the operating section 14, or that where notification of the achievement status is instructed, for example, by pressing an achievement status display button included in the operating section 14.

In the case where the biological information measurement device 1 is operated by batteries, a determination condition that the remaining battery power of the biological information measurement device 1 is equal to or smaller than a predetermined remaining threshold which is necessary for the operation of measuring biological information may be employed.

The scheduled-visit-day change determining section 11C acquires the information of the scheduled hospital visit day which is stored in the storage medium 13, and determines whether the scheduled next hospital visit day is required to be changed or not, based on the acquired information of the scheduled hospital visit day, and the achievement status that is determined by the achievement status determining section 11B.

For example, the description will be made by exemplifying a case where the condition stored in the storage medium 13 is the second condition (the condition "The number of groups of biological information for one day which are stored in the storage medium 13 from the arbitrary timing functioning as the reference becomes equal to or larger than the threshold TH2"). Here, the threshold TH2 in the second condition is assumed to be "7".

It is assumed that, at the timing when the achievement status determining section 11B determines the achievement status, the number of groups for one day which are contained in biological information that has already stored in the storage medium 13 is five as compared to groups of biological information for seven days which are necessary for diagnosis.

In this case, it can be determined that measurement of biological information for at least two days is necessary until the second condition is achieved. The scheduled-visit-day change determining section 11C calculates the number of days (the number of days remaining until the scheduled hospital visit day) which exist from the date when the achievement status determining section 11B determines the achievement status, to the date of the scheduled hospital visit day, and compares the calculated number of days remaining until the scheduled hospital visit day with the minimum number of the days which are necessary for achieving the second condition (in the above example, two days).

If the number of days remaining until the scheduled hospital visit day exceeds the minimum number of the days which are necessary for achieving the second condition, then, the scheduled-visit-day change determining section 11C determines that the scheduled hospital visit day is not required to be changed. If the number of days remaining until the scheduled hospital visit day is equal to or smaller than the minimum number of the days which are necessary for achieving the second condition, the scheduled-visit-day change determining section 11C determines that the scheduled hospital visit day is required to be changed.

The notification processing section 11D performs a process of notifying of the achievement status which is determined by the achievement status determining section 11B.

This process is a process of displaying information based on the achievement status on the displaying section 15, that of outputting the information based on the achievement status in the form of a sound output from a speaker of the biological information measurement device 1 which is not shown, that of transmitting the information based on the achievement status from the communication interface (I/F) 12 to an external electronic device (for example, a smartphone possessed by the subject), or the like.

The notification processing section 11D performs also a process of notifying of information based on the result of the determination performed by the scheduled-visit-day change determining section 11C.

Figure 3:
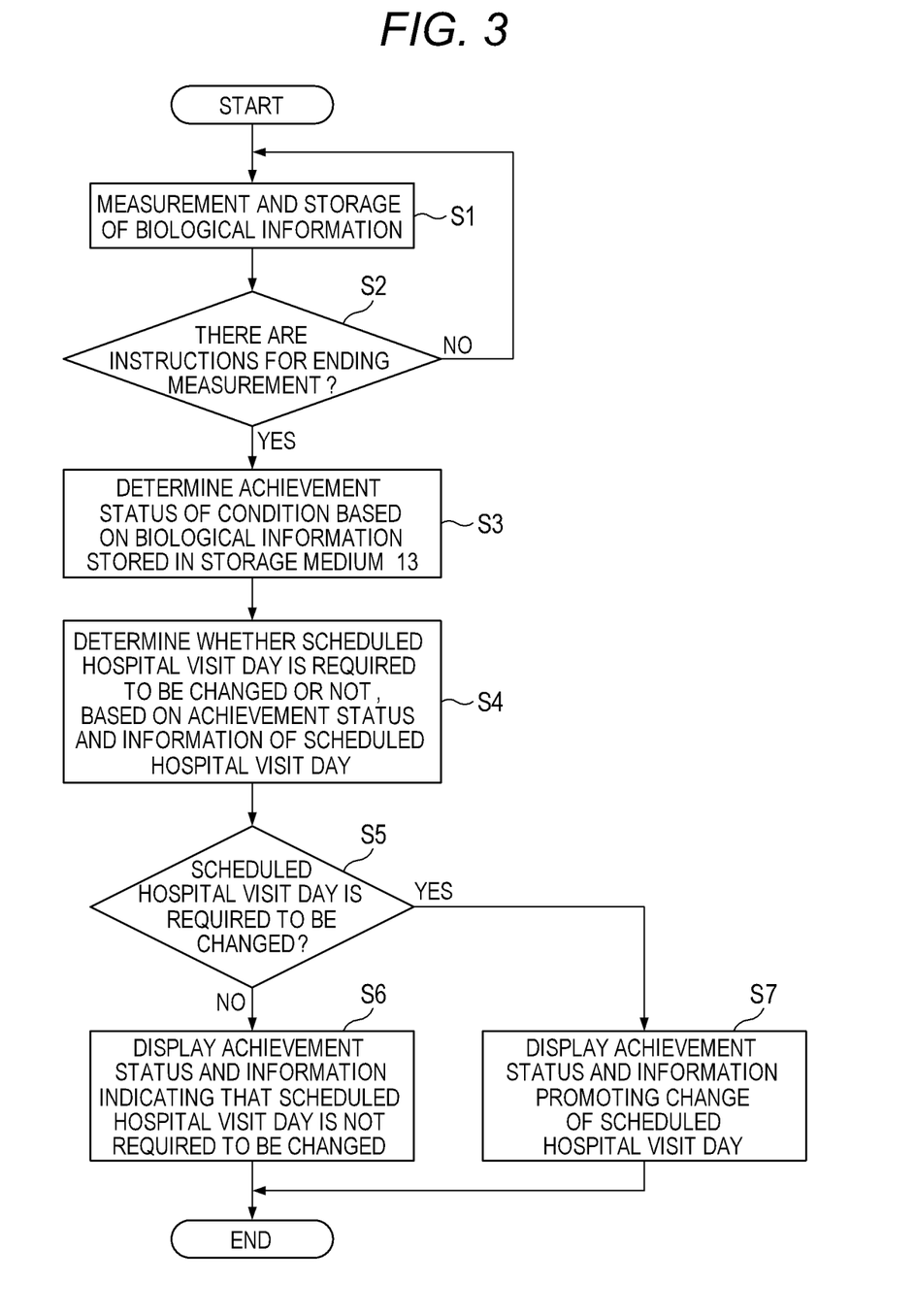
FIG. 3 is a flowchart illustrating the operation of the biological information measurement device 1 shown in FIG. 1.

FIG. 3 is a flowchart illustrating an example of the operation of the biological information measurement device 1 shown in FIG. 1. Here, a case where the notification processing section 11D performs notification by causing the displaying section 15 to display information will be described. The description will be made while assuming that the determination condition is the condition that the end of the measurement of biological information is instructed.

When the biological information measurement device 1 is attached to the subject, and a measurement start button included in the operating section 14 is depressed, the biological information calculating section 11A of the system controller 11 calculates biological information based on the pulse wave detected by the pulse wave detecting section 10, and causes the calculated biological information to be stored in the storage medium 13 (step S1).

After the start of the measurement of biological information, the achievement status determining section 11B of the system controller 11 determines whether instructions for ending the measurement of biological information is input or not (step S2). If the instructions for ending the measurement are not input (step S2: NO), the process returns to step S1.

If the instructions for ending the measurement are input (step S2: YES), the achievement status determining section 11B determines the achievement status of the condition stored in the storage medium 13 (here, assumed that the second condition is stored), based on biological information which is among the biological information stored in the storage medium 13, and which is stored on or after the arbitrary timing functioning as the reference (step S3).

Next, the scheduled-visit-day change determining section 11C of the system controller 11 acquires the information of the scheduled hospital visit day which is stored in the storage medium 13, and determines whether the scheduled next hospital visit day for the subject is required to be changed or not, based on the acquired information of the scheduled hospital visit day, and the achievement status that is determined in step S3 (step S4).

If it is determined in step S4 that the scheduled hospital visit day is required to be changed (step S5: YES), the notification processing section 11D causes information based on the achievement status which is determined in step S3, and information promoting a change of the scheduled hospital visit day to be displayed on the displaying section 15 (step S7).

Figure 4A:
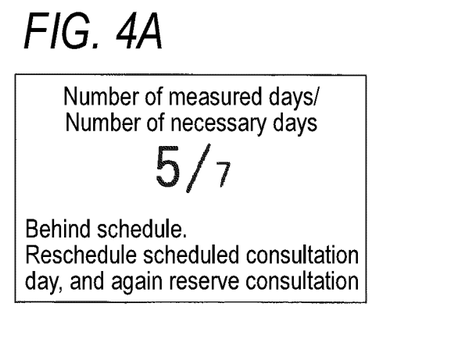
FIGS. 4A to 4G is a view showing screen display examples of a displaying section 15 of the biological information measurement device 1 shown in FIG. 1.

FIG. 4A is a view showing an example of a screen which is displayed on the displaying section 15 in step S7. In FIG. 4A, a screen example in the case where the threshold TH2 of the second condition which is used in the determination of the achievement status in step S3 is "7" is shown.

As shown in FIG. 4A, an item "Number of measured days/Number of necessary days" and characters "5/7" which is a result corresponding to the item are displayed as information based on the achievement status on the displaying section 15. The numerical value "5" corresponds to the number of the measured days, and the numerical value "7" corresponds to the number of the necessary days. "Number of measured days" indicates the number of groups of biological information for one day, and "Number of necessary days" indicates the threshold TH2. Moreover, a message promoting a change of the scheduled hospital visit day, i.e., "Behind schedule. Reschedule scheduled consultation day, and again reserve consultation." is displayed as information promoting a change of the scheduled hospital visit day, on the displaying section 15.

If it is determined in step S4 that the scheduled hospital visit day is not required to be changed (step S5: NO), the notification processing section 11D causes information based on the achievement status which is determined in step S3, and information indicating that the scheduled hospital visit day is not required to be changed, to be displayed on the displaying section 15 (step S6).

Figure 4B:
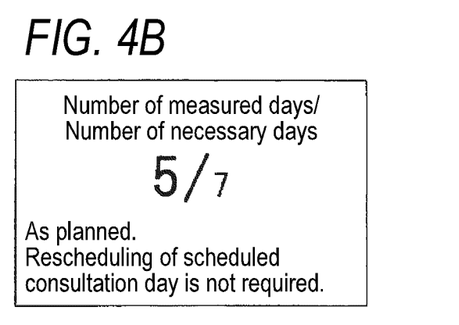

FIG. 4B is a view showing an example of a screen which is displayed on the displaying section 15 in step S6. In FIG. 4B, a screen example in the case where the threshold TH2 of the second condition which is used in the determination of the achievement status in step S3 is "7" is shown.

Figure 4C:
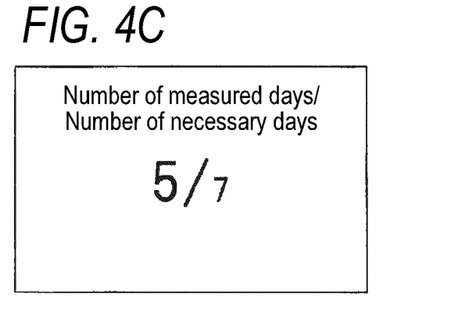

As shown in FIG. 4B, the information identical with that of FIG. 4A is displayed as information based on the achievement status, on the displaying section 15. Moreover, a message "As planned. Rescheduling of scheduled consultation day is not required." is displayed as information indicating that the scheduled hospital visit day is not required to be changed, on the displaying section 15. As shown in FIG. 4C, alternatively, the notification processing section 11D may cause only information based on the achievement status to be displayed in step S6 on the displaying section 15.

FIGS. 4D to 4G are views showing display examples of information which is displayed in step S6 or step S7 on the displaying section 15, and which is based on the achievement status.

Figure 4D:
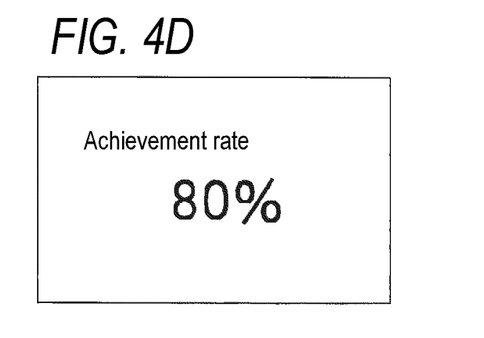
Figure 4E:
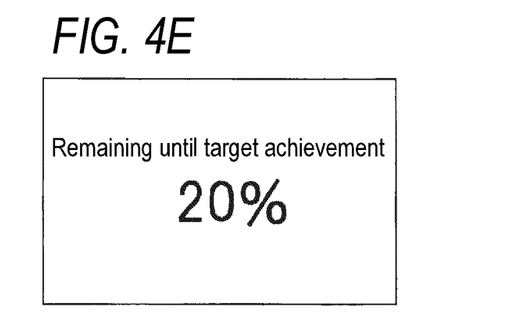
Figure 4F:
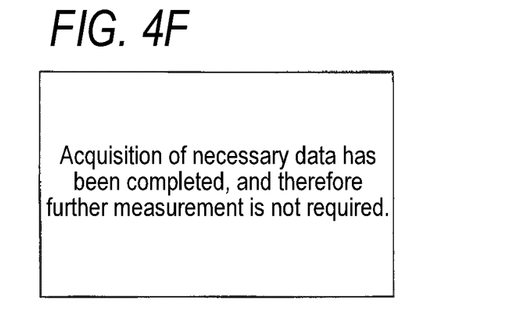

FIGS. 4D and 4E show screen display examples in the case where the achievement rate determined by the achievement status determining section 11B is 80%. FIG. 4F shows a screen display example in the case where the achievement rate determined by the achievement status determining section 11B is 100%.

The achievement rate in the case where the first condition is employed is a rate with respect to the threshold TH1 of the total number of sets of biological information stored in the storage medium 13. The upper limit of the rate is 100%.

The achievement rate in the case where the second condition is employed is a rate with respect to the threshold TH2 of the total number of groups of biological information for one day which are stored in the storage medium 13. The upper limit of the rate is 100%.

The achievement rate in the case where the third condition is employed is a rate with respect to the threshold TH3 of the occurrence frequency of the first pattern based on the biological information stored in the storage medium 13. The upper limit of the rate is 100%.

The achievement rate in the case where the fourth condition is employed is a rate with respect to the threshold TH4 of the number of occurrences of the specific pattern based on the biological information stored in the storage medium 13. The upper limit of the rate is 100%.

As shown in FIG. 4D, the notification processing section 11D may cause information indicating the achievement rate to be displayed as it is on the displaying section 15.

As shown in FIG. 4E, the notification processing section 11D may cause information indicating the remaining rate which is obtained from the achievement rate, and which is necessary for achieving the condition, to be displayed on the displaying section 15.

In the case where the achievement rate is 100%, the notification processing section 11D may cause a message such as shown in FIG. 4F as information indicating that it is not necessary to further measure biological information, to be displayed.

Figure 4G:
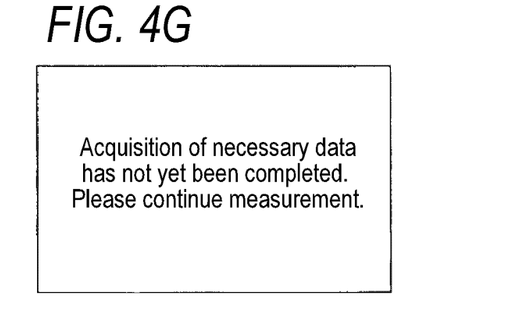

In the case where the achievement rate is smaller than 100%, the notification processing section 11D may cause a message such as shown in FIG. 4G as information indicating that it is necessary to continue the measurement of biological information, to be displayed.

Figure 5A:
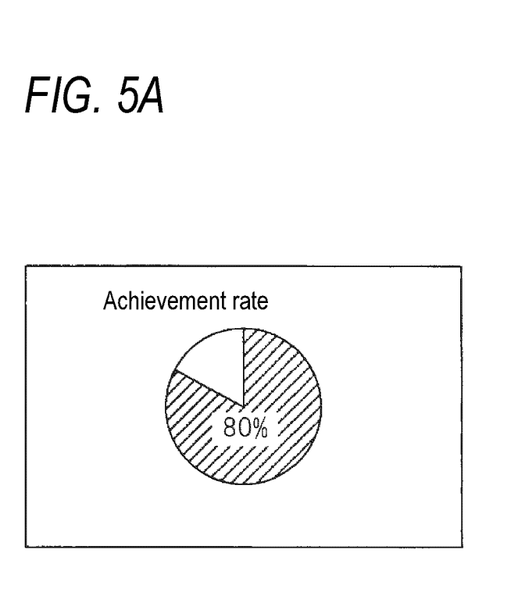
FIGS. 5A and 5B is a view showing screen display examples of the displaying section 15 of the biological information measurement device 1 shown in FIG. 1.
Figure 5B:
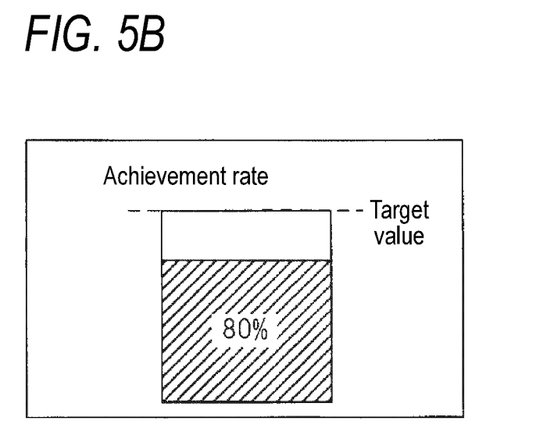

As shown in FIGS. 5A and 5B, the notification processing section 11D notifies of the achievement status by means of not only a message but also graphics such as a circle graph or a bar graph.

As described above, in the case where the end of the measurement of biological information is instructed, for example, the biological information measurement device 1 determines the achievement status of the condition for biological information based on the biological information in the storage medium 13, and notifies of the determined achievement status. From the notified achievement status, therefore, the subject can easily know whether information which is necessary until the next consultation is stored in the storage medium 13, or not. Consequently, a situation where consultation in the hospital is performed in a state where information is insufficient can be prevented from occurring, and the doctor can efficiently diagnose the subject.

According to the biological information measurement device 1, the subject is notified of the necessity or unnecessity of a change of the scheduled hospital visit day, based on the achievement status and information of the scheduled hospital visit day. Therefore, a situation where consultation is performed in a state where information is insufficient can be prevented at a high degree of certainty from occurring.

The scheduled-visit-day change determining section 11C of the system controller 11 is not an essential component, and may be omitted. In this case, the biological information measurement device 1 operates in the following manner. In the flowchart shown in FIG. 3, steps S4 to S7 are deleted, and, after step S3, a screen containing information based on the achievement status (for example, the screens shown in FIGS. 4C to 4G) is displayed on the displaying section 15.

In the case where the end of the measurement of biological information is instructed, for example, the biological information measurement device 1 notifies of the achievement status. Therefore, the possibility that the subject misses the achievement status can be reduced as far as possible, and efficient measurement can be performed. This is because it is considered that, after measurement is ended, the subject certainly views the displaying section 15 and the like.

In the biological information measurement device 1, in the case where the remaining battery power of the biological information measurement device 1 is equal to or smaller than the remaining threshold which is necessary for the operation of measuring biological information, notification of the achievement status is performed. Depending on the contents of the notification, therefore, the subject can determine whether the device is further charged from the present time to continue measurement or not, and it is possible to eliminate a waste charging work.

In the biological information measurement device 1, in the case where notification of the achievement status is instructed, the achievement status is notified. Therefore, the subject can check the achievement status at an arbitrary timing. Consequently, this can contribute to enhanced motivation to measure biological information, and eliminate waste measurement.

Figure 6:
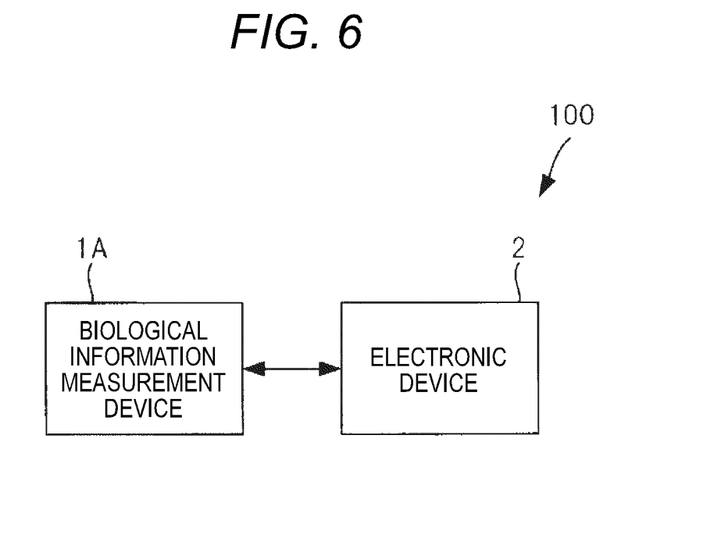
FIG. 6 is a diagram schematically showing the configuration of a diagnosis assistance system 100 which is an embodiment of the invention.

FIG. 6 is a diagram schematically showing the configuration of a diagnosis assistance system 100 which is an embodiment of the invention. The diagnosis assistance system 100 includes a biological information measurement device 1A and an electronic device 2.

The internal hardware configuration of the biological information measurement device 1A is identical with that of the biological information measurement device 1, and therefore its description is omitted. The functional block diagram of the system controller 11 of the biological information measurement device 1A is formed by deleting the achievement status determining section 11B, the scheduled-visit-day change determining section 11C, and the notification processing section 11D from FIG. 2.

The electronic device 2 is an electronic device such as a personal computer, a smartphone, or a tablet terminal.

The electronic device 2 can be wiredly or wirelessly connected to the biological information measurement device 1A, and read data of the storage medium 13 of the biological information measurement device 1A. In the case where the storage medium 13 of the biological information measurement device 1A is of the portable type, the electronic device 2 may have means by which data can be read from the storage medium, and be configured so as to read data from an attached storage medium.

Figure 7:
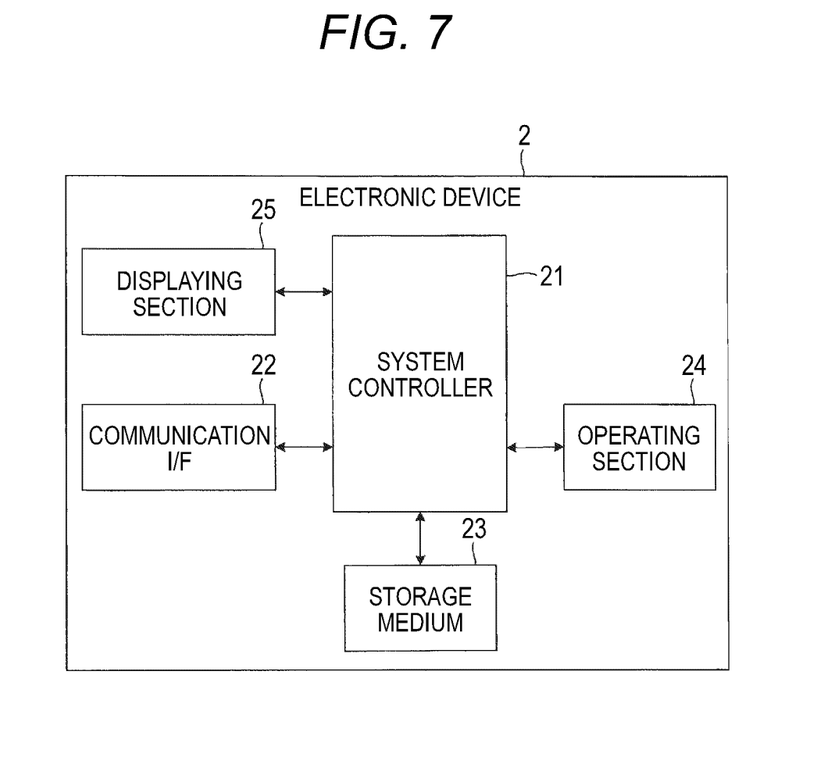
FIG. 7 is a diagram showing the internal hardware configuration of an electronic device 2 of the diagnosis assistance system 100 shown in FIG. 6.

FIG. 7 is a diagram showing the internal hardware configuration of the electronic device 2 of the diagnosis assistance system 100 shown in FIG. 6.

The electronic device 2 includes a system controller 21 which generally controls the entire device, a communication interface (I/F) 22, a storage medium 23, an operating section 24, and a displaying section 25.

The system controller 21 is configured mainly by a processor, and includes a ROM which stores programs and the like to be executed by the processor, a RAM functioning as a work memory, and the like.

The communication I/F 22 is an interface for wiredly or wirelessly connecting the device to other electronic devices including the biological information measurement device 1A.

The storage medium 23 stores data which are read out from the biological information measurement device 1A. The storage medium 23 is configured by, for example, a flash memory.

The operating section 24 is an interface for inputting an instruction signal for the system controller 21, and configured by a keyboard, a mouse, buttons, a touch panel, or the like.

The displaying section 25 is used for displaying various information, and configured by a liquid crystal display device or the like.

Figure 8:
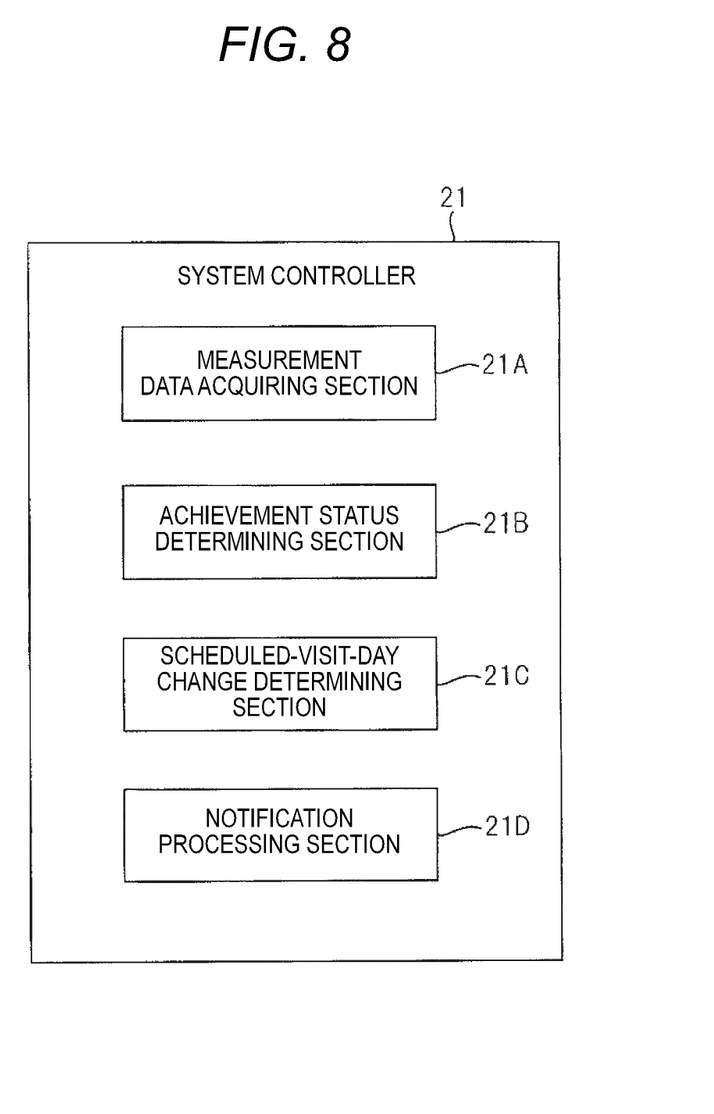
FIG. 8 is a functional block diagram of a system controller 21 of the electronic device 2 shown in FIG. 7.

FIG. 8 is a functional block diagram of the system controller 21 of the electronic device 2 shown in FIG. 7.

The system controller 21 includes a measurement data acquiring section 21A, an achievement status determining section 21B, a scheduled-visit-day change determining section 21C, and a notification processing section 21D.

The measurement data acquiring section 21A, the achievement status determining section 21B, the scheduled-visit-day change determining section 21C, and the notification processing section 21D are configured by causing the processor to execute the programs stored in the ROM. The programs include the diagnosis assistance program. The system controller 21 constitutes the diagnosis assistance device.

The measurement data acquiring section 21A acquires, from the storage medium 13 of the biological information measurement device 1A, various data containing biological information stored in the storage medium 13 (including information of conditions for biological information, and that of the scheduled hospital visit day), and causes the data to be stored in the storage medium 23.

The achievement status determining section 21B has functions which are similar to those of the achievement status determining section 11B, and determines the achievement status of the condition which is stored in the storage medium 23, based on biological information which is among the biological information stored in the storage medium 13, and which is stored on or after the arbitrary timing, at a timing when the operating section 24 of the electronic device 2 is operated, and notification of the achievement status is instructed, that when copying of the data on the storage medium 13 to the storage medium 23 is completed, or the like timing.

The scheduled-visit-day change determining section 21C has functions which are similar to those of the scheduled-visit-day change determining section 11C, and determines whether the scheduled hospital visit day is required to be changed or not, based on the achievement status that is determined by the achievement status determining section 21B, and the information of the scheduled hospital visit day stored in the storage medium 23.

The notification processing section 21D has functions which are similar to those of the notification processing section 11D, and performs a process of notifying of information based on the achievement status which is determined by the achievement status determining section 21B, and information of the necessity or unnecessity of a change of the scheduled hospital visit day which is determined by the scheduled-visit-day change determining section 21C. The notification processing section 21D performs notification by causing the information to be displayed on the displaying section 25, or outputting a sound from a speaker which is not shown.

As described above, also the configuration where the electronic device 2 determines the achievement status of the condition, and the necessity or unnecessity of a change of the scheduled hospital visit day, and notifies of the information is possible. According to the configuration, the throughput in the biological information measurement device 1A can be reduced, and the battery life of the device can be prolonged. Even in the case where the displaying section, the speaker, or the like are not disposed in the biological information measurement device 1A, moreover, the achievement status and the like can be notified to the subject, and the configuration can cope with miniaturization and cost reduction of the biological information measurement device 1A.

Although, in the above description, the biological information measurement device 1 and the biological information measurement device 1A are assumed to calculate biological information for each beat based on the pulse wave which is a biological signal detected by the pulse wave detecting section 10, the method for measuring biological information, or the measurement frequency of biological information is not limited to the above, and well known techniques may be employed.

For example, the biological information measurement device 1 and the biological information measurement device 1A may have a configuration where a device for measuring the pulse wave propagation velocity is used in place of the pulse wave detecting section 10, and biological information such as blood pressure information is calculated for each beat based on the pulse wave propagation velocity which is a biological signal detected by the device.

The biological information measurement device 1 and the biological information measurement device 1A may calculate blood pressure information, pulse information, or beat information by using the oscillometric method or the like, and cause the information to be stored in the storage medium 13. The measurement of biological information may be performed at a timing which is designated by the doctor (for example, morning, daytime, and night, or every hour).

Although the notification processing section 11D and the notification processing section 21D basically notify the achievement status to the subject of the biological information measurement device 1 and the biological information measurement device 1A, the sections may have a configuration where information based on the achievement status is transmitted to a terminal of the hospital to which the subject regularly visits, through the Internet or the like, and a person concerned with the hospital is notified of the achievement status.

According to the configuration, the measurement status of the patient can be known on the side of the hospital, and a countermeasure such as prompting the patient to change the appointment day can be taken. As a result, the diagnosis can be efficiently performed.

The notification processing section 11D and the notification processing section 21D may notify the subject or a person concerned with the hospital of the achievement status, every predetermined period such as one day. According to this, effects that, even when the subject does not perform a specific operation, the achievement status can be informed by push, and that, in a situation where the number of samples of biological information is insufficient, the subject is encouraged for improvement can be expected. A person concerned with the hospital may provide the subject with an advice for promoting improvement.

In the case where the above-described condition (the first to fifth conditions) is achieved, the notification processing section 11D and the notification processing section 21D may notify the subject or a person concerned with the hospital of the situation where the condition is achieved.

The above-described various programs are stored in a non-transitory recording medium from which a computer can read the programs.

For example, such "computer readable recording medium" includes a ROM, an optical medium such as a CD-ROM (Compact Disc-ROM), a magnetic recording medium such as a memory card, and the like. Alternatively, such programs can be provided by downloading via a network.

The presently disclosed embodiments should be considered in all respects to be illustrative and not restrictive. The scope of the invention is indicated by the appended claims rather than the foregoing description, and all changes which come within the meaning and range of the claims and equivalents thereof are intended to be embraced therein.

As described above, the following matters are disclosed in the specification.

There is disclosed a diagnosis assistance device for assisting a diagnosis which is performed by using a plurality of sets of biological information that are measured from a subject, and that are stored in a storage medium, the diagnosis assistance device comprising:

an achievement status determining section which determines an achievement status of a predetermined condition related to biological information that is measured from the subject, based on the plurality of sets of biological information stored in the storage medium; and a notification processing section which performs a process of notifying of the achievement status.

The disclosed diagnosis assistance device may be configured such that the condition is a condition related to a number of the sets of biological information which are stored in the storage medium.

The disclosed diagnosis assistance device may be configured such that the condition is that the number of the sets of biological information which are stored in the storage medium is equal to or larger than a threshold.

The disclosed diagnosis assistance device may be configured such that the condition is that a number of groups of biological information for one day which are stored in the storage medium is equal to or larger than a threshold.

The disclosed diagnosis assistance device may be configured such that the condition is a condition related to a pattern of a change of biological information which is stored in the storage medium.

The disclosed diagnosis assistance device may be configured such that the condition is that, in the biological information stored in the storage medium, an occurrence frequency of a pattern in which the biological information temporarily rises to or higher than a reference value is equal to or larger than a threshold.

The disclosed diagnosis assistance device may be configured such that the condition is that the pattern of a change of biological information which is stored in the storage medium contains, threshold or more times, a specific pattern.

The disclosed diagnosis assistance device may be configured such that the specific pattern is a pattern in which the biological information temporarily rises to or higher than a reference value, or a pattern in which a variation amount of the biological information is temporarily equal to or larger than a threshold.

The disclosed diagnosis assistance device may be configured such that the specific pattern is extreme-dipper, non-dipper, or riser.

The disclosed diagnosis assistance device may be configured such that the condition is that the biological information which is stored in the storage medium contains information in which an absolute value is equal to or larger than a threshold.

The disclosed diagnosis assistance device may be configured such that the biological information is blood pressure information.

There is disclosed a biological information measurement device which measures biological information, and which stores the biological information in a storage medium, wherein the biological information measurement device includes the diagnosis assistance device.

The disclosed biological information measurement device may be configures such that, in a case where an end of the measurement of biological information is instructed, a case where a remaining battery power of the biological information measurement device is equal to or smaller than a predetermined remaining threshold which is necessary for an operation of measuring biological information, or a case where notification of an achievement status is instructed, the notification processing section notifies of the achievement status.

The disclosed biological information measurement device may be configures such that the notification processing section notifies of the achievement status, every predetermined period.

The disclosed biological information measurement device may be configures such that the device further includes a scheduled-visit-day change determining section which acquires information of a scheduled hospital visit day of the subject from a storage medium that stores the information of the scheduled hospital visit day, and which determines whether the scheduled hospital visit day is required to be changed or not, based on the information and the achievement status, and the notification processing section further notifies of a result of the determination by the scheduled-visit-day change determining section, in addition to the achievement status.

The disclosed biological information measurement device may be configures such that, in a case where the condition is achieved, the notification processing section notifies of information indicating that the condition is achieved.

The disclosed biological information measurement device may be configures such that the device includes a biological information calculating section which calculates biological information for each beat based on a biological signal detected from the subject.

There is disclosed a diagnosis assistance method for assisting a diagnosis which is performed by using a plurality of sets of biological information that are measured from a subject by a biological information measurement device, and that are stored in a storage medium, the diagnosis assistance method including:

an achievement status determining step of determining an achievement status of a predetermined condition related to biological information that is measured from the subject, based on the plurality of sets of biological information stored in the storage medium; and a notification processing step of performing a process of notifying of the achievement status.

There is disclosed a diagnosis assistance program for assisting a diagnosis which is performed by using a plurality of sets of biological information that are measured from a subject by a biological information measurement device, and that are stored in a storage medium, wherein
the program causes a computer to execute:

an achievement status determining step of determining an achievement status of a predetermined condition related to biological information that is measured from the subject, based on the plurality of sets of biological information stored in the storage medium; and a notification processing step of performing a process of notifying of the achievement status.

The invention is very convenient and effective particularly in application to a blood pressure monitor or the like.

Although the invention has been described with reference to the specific embodiments, the invention is not limited to the embodiments, and various changes can be made without departing from the technical spirit of the disclosed invention.

According to the invention, it is possible to provide a diagnosis assistance device, biological information measurement device, diagnosis assistance method, and diagnosis assistance program which enable the subject to check whether information necessary for a diagnosis is accumulated or not, and which can assist a prompt and correct diagnosis.

What is claimed is:

1. A diagnosis assistance device for assisting a diagnosis which is performed by using biological information that is measured from a subject, and that is stored in a storage medium, the diagnosis assistance device comprising:
   a processor programmed to:
   receive the biological information from a sensor connected to the subject and control the storage medium to store the received biological information;
   determine whether a predetermined condition related to the biological information that is measured from the subject is satisfied, based on the biological information stored in the storage medium;
   determine (i) an amount of additional time required to acquire an additional amount of the biological information necessary to satisfy the predetermined condition or (ii) an achievement rate indicating an amount of the biological information necessary to satisfy the predetermined condition that has already been acquired; and
   control a display or a speaker to notify the subject of the amount of additional time or the achievement rate,
   wherein the predetermined condition is that a pattern of a change of the biological information that is stored in the storage medium contains a threshold or more times a specific pattern, and
   the specific pattern is extreme-dipper, non-dipper, or riser.

2. The diagnosis assistance device according to claim 1, wherein the biological information is blood pressure information.

3. A biological information measurement device that measures biological information comprising:
   a sensor configured to detect the biological information from a subject;
   a storage medium that stores the detected biological information;
   a processor programmed to:
   determine whether a predetermined condition related to the biological information that is measured from the subject is satisfied, based on biological information stored in the storage medium;
   determine (i) an amount of additional time required to acquire an additional amount of the biological information necessary to satisfy the predetermined condition or (ii) an achievement rate indicating an amount of the biological information necessary to satisfy the predetermined condition that has already been acquired;
   control a display or a speaker to notify the subject of the amount of additional time or the achievement rate;

acquire information of a scheduled hospital visit day of the subject that is stored in the storage medium, and determine whether the scheduled hospital visit day is required to be changed or not, based on (i) the acquired information and (ii) the amount of additional time or the achievement rate; and notify the subject as to whether the scheduled hospital visit day is required to be changed or not.

4. The biological information measurement device according to claim 3, wherein, in a case where an end of the measurement of biological information is instructed, a case where a remaining battery power of the biological information measurement device is equal to or smaller than a predetermined remaining threshold which is necessary for an operation of measuring biological information, or a case where notification of an achievement status is requested by the subject, the processor is programmed to notify the subject of the amount of additional time, or the achievement rate.

5. The biological information measurement device according to claim 3, wherein the processor is further programmed to notify the subject of the amount of additional time, or the achievement rate, multiple times.

6. The biological information measurement device according to claim 3, wherein the sensor detects pulse information as the biological information, and the processor is further programmed to calculate information for each heartbeat based on the pulse information detected from the subject.

7. A diagnosis assistance method for assisting a diagnosis which is performed by using biological information that is measured from a subject by a biological information measurement device, and that is stored in a storage medium, the diagnosis assistance method comprising:

receiving the biological information from a sensor connected to the subject and controlling the storage medium to store the received biological information;

determining that a predetermined condition related to the biological information that is measured from the subject is not satisfied, based on the biological information stored in the storage medium;

determining (i) an amount of additional time required to acquire an additional amount of the biological information necessary to satisfy the predetermined condition or (ii) an achievement rate indicating an amount of the biological information necessary to satisfy the predetermined condition that has already been acquired; and controlling a display or a speaker to notify the subject of the amount of additional time or the achievement rate, wherein the predetermined condition is that a pattern of a change of the biological information that is stored in the storage medium contains a threshold or more times a specific pattern, and the specific pattern is extreme-dipper, non-dipper, or riser.

8. A non-transitory computer-readable storage medium, which includes a diagnosis assistance program for assisting a diagnosis which is performed by using biological information that is measured from a subject by a biological information measurement device, wherein the program causes a computer to execute a process comprising:

receiving the biological information from a sensor connected to the subject and controlling the storage medium to store the received biological information;

determining that a predetermined condition related to the biological information that is measured from the subject is not satisfied, based on the biological information stored in the storage medium; and determining (i) an amount of additional time required to acquire an additional amount of the biological information necessary to satisfy the predetermined condition or (ii) an achievement rate indicating an amount of the biological information necessary to satisfy the predetermined condition that has already been acquired; and controlling a display or a speaker to notify the subject of the amount of additional time or the achievement rate, wherein the predetermined condition is that a pattern of a change of the biological information that is stored in the storage medium contains a threshold or more times a specific pattern, and the specific pattern is extreme-dipper, non-dipper, or riser.

* * * * *